United States Patent
Isaka (10) Patent No.: US 6,649,786 B2
(45) Date of Patent: Nov. 18, 2003

(54) ESTER-FORMING ADDITION REACTION PRODUCT

(75) Inventor: Hisashi Isaka, Atsugi (JP)

(73) Assignee: Kansai Paint Co., Ltd., Hyogo-ken (JP)

(*) Notice: Subject to any disclaimer, the term of this patent is extended or adjusted under 35 U.S.C. 154(b) by 0 days.

(21) Appl. No.: 10/224,426

(22) Filed: Aug. 21, 2002

(65) Prior Publication Data

US 2003/0069439 A1 Apr. 10, 2003

(30) Foreign Application Priority Data

Aug. 21, 2001 (JP) ........................................ 2001-250146

(51) Int. Cl.[7] .............................................. C07C 69/66
(52) U.S. Cl. ....................... 560/186; 528/297; 560/199; 560/200
(58) Field of Search ........................... 528/297; 560/186, 560/199, 200

(56) References Cited

U.S. PATENT DOCUMENTS

| | | | |
|---|---|---|---|
| 4,314,918 A | * | 2/1982 | Birkmeyer et al. |
| 5,693,723 A | | 12/1997 | Green |
| 5,952,452 A | * | 9/1999 | Aerts et al. ................. 528/297 |
| 6,069,203 A | * | 5/2000 | Henry et al. ................. 525/131 |

* cited by examiner

*Primary Examiner*—Alan L. Rotman
*Assistant Examiner*—Hector M. Reyes
(74) *Attorney, Agent, or Firm*—Wenderoth, Lind&Ponack, LLP (57) ABSTRACT

This invention provides a process to produce a hydroxyl group-containing ester-forming addition reaction product having an acid value of 20 mgKOH/g or less, which process is characterized in that 2,2-dimethylolalkanoic acid having 6 to 8 carbon atoms is melted, and is then mixed with alkanoic acid monoglycidylester having 8 to 24 carbon atoms so that an ester-forming addition reaction may occur. Thus obtained reaction product contains almost no undesirable high-molecular components, is quite excellent in reactivity and compatibility with a curing agent, and is useful for the manufacture of high-solids paint etc.

11 Claims, 3 Drawing Sheets

Decomposition 4cm$^{-1}$
Number of integration 16
Apodization Cosine

ESTER-FORMING ADDITION REACTION PRODUCT

This invention relates to an ester-forming addition reaction product which is useful for the manufacture of low-solvent or non-solvent articles in the field of paint, ink, adhesive, etc., and which is excellent both in compatibility with curing agent and in curability. This invention also relates to a process for the production of said product.

From environmental concerns, the manufacture of low-solvent articles has recently been being promoted in the field of paint, ink, adhesive, etc. As one of the means to achieve this purpose, the utilization of reactive diluent is being considered. Furthermore, paint and ink which comprise, as main components, low-molecular compounds such as reactive diluent or oligomer are also being studied with a view to attaining much lower-solvent or non-solvent articles.

For instance, U.S. Pat. No. 4,314,918 discloses an idea of blending, with a coating composition, a reactive diluent which has a functionality of at least 2.0, an acid number of less than 50 mgKOH/g, a non-volatile content of greater than about 85% and a Gardner-Holdt viscosity of less than $Z_{10}$. U.S. Pat. No. 5,952,452 and U.S. Pat. No. 6,069,203 exemplify a hydroxyl group-containing oligomer (polyesterpolyol oligomer, oligoether) to be blended with a high solids coating composition, which oligomer is manufactured from a reaction of branched fatty glycidyl ester.

The reactive diluent and oligomer which are disclosed in the above-mentioned U.S. patents have, owing to their production process, no selectivity in reacting with a number of functional groups, and, therefore, components are formed more than intended from the reaction, and the polydispersibility (ratio of weight average molecular weight to number average molecular weight) of molecular weight distribution increases, and, resultantly, the viscosity of products increases, which is disadvantageous for the manufacture of low-solvent articles.

In detail, (1) in a combination of polyol and glycidylester or glycidylether (hereinafter referred to as glycidylester/ether), hydroxyl group in polyol has no selectivity, and, therefore, there are formed undesirable components from a reaction of polyol with a number of glycidylester/ether; (2) in a combination of polyol and acid anhydride, hydroxyl group in polyol has similarly no selectivity, and, therefore, there are formed undesirable components from a reaction of polyol with a number of acid anhydrides; and (3) in a combination of oxyacid which has a high melting point and glycidylester/ether, a reaction needs to be conducted at a high temperature, and, therefore, a reaction between hydroxyl group and carboxyl group partially occurs in addition to the intended reaction between glycidyl group and carboxyl group, and, thus, there are formed undesirable high-molecular components.

As for polyether polyol and polycaprolactone polyol which are known well as reactive diluent, they have a problem that the hardness of cured matters decreases, and that they are inferior in compatibility with curing agent, as well as the above-mentioned problem that high-molecular components are formed.

The objective of this invention is to provide a hydroxyl group-containing ester-forming addition reaction product which contains almost no undesirable high-molecular components, which is excellent in reactivity and compatibility, and which is useful for the manufacture of low-solvent or high-solid articles such as paint, ink, adhesive, etc., and to provide a process for the production of said hydroxyl group-containing ester-forming addition reaction product.

The inventors studied assiduously for the purpose of attaining the above-mentioned objectives, and have now found that a product of an ester-forming addition reaction between 2,2-dimethylolalkanoic acid having 6 to 8 carbon atoms which is an oxyacid having comparatively low melting point and alkanoic acid monoglycidylester having a hydrophobic group is not only useful for the manufacture of low-solvent or high-solid articles, but also is a material which is excellent in curability and compatibility. The inventors have further found an efficient process for the production of said product, and have thus completed this invention.

This invention provides a product of ester-forming addition reaction between 2,2-dimethylolalkanoic acid of the following formula (I):

(I)

wherein $R^2$ is an alkyl group having 2 to 4 carbon atoms, and alkanoic acid monoglycidylester of the following formula (II):

(II)

wherein $R^1$ is an alkyl group having 4 to 20 carbon atoms, which product has an acid value of 20 mgKOH/g or less.

This invention also provides a process to produce the above-mentioned ester-forming addition reaction product, which process is characterized in that an ester-forming addition reaction is conducted between 2,2-dimethylolalkanoic acid of the following formula (I):

(I)

wherein $R^2$ is an alkyl group having 2 to 4 carbon atoms, and alkanoic acid monoglycidylester of the following formula (II):

(II)

wherein $R^1$ is an alkyl group having 4 to 20 carbon atoms, until the acid value of the resultant reaction product becomes 20 mgKOH/g or less.

In the following, this invention is explained in more detail.

One of the characteristic features of this invention is to use 2,2-dimethylolalkanoic acid having 6 to 8 carbon atoms such as 2,2-dimethylolbutanoic acid. This compound has, in a molecule, plural functional groups which are different in reactivity, i.e., two hydroxyl groups and one carboxyl group. By an ester-forming addition reaction between this carboxyl group of dimethylolalkanoic acid and alkanoic acid monoglycidylester, any desired hydroxyl group-containing ester-forming addition reaction product can easily be synthesized.

There has been publicly known (see, e.g., U.S. Pat. No. 4,314,918 and U.S. Pat. No. 5,693,723) a process per se for producing polyol by a reaction between oxyacid having, in a molecule, hydroxyl group and carboxyl group, and alkanoic acid monoglycidylester.

Oxyacids which have conventionally been used are, however, glycolic acid, lactic acid, hydroxy pivalic acid, 12-hydroxy stearic acid, malic acid, citric acid, tartaric acid, 2,2-dimethylolpropionic acid, etc. Among these oxyacids, glycolic acid, lactic acid, hydroxy pivalic acid and 12-hydroxy stearic acid have only a single hydroxyl group in a molecule, and, therefore, diol is formed from an ester-forming addition reaction with alkanoic acid monoglycidylester. As a result, there occurs a problem that, when the product from said ester-forming addition reaction is used in a large amount, curability decreases. Furthermore, for instance, malic acid, citric acid and tartaric acid have plural carboxl groups, which fact causes a problem of selectivity in reaction. Besides, 2,2-dimethylolpropionic acid has a melting point as high as 150° C., which gives rise to a problem that, during an ester-forming addition reaction with glycidyl group at a high temperature, there are liable to occur, as a subsidiary reaction, a reaction between carboxyl group and hydroxyl group and a reaction between hydroxyl group and glycidyl group.

In this invention, 2,2-dimethylolalkanoic acid having 6 to 8 carbon atoms and having low melting point which is represented by 2,2-dimethylolbutanoic acid having a melting point of 110° C. is subjected, as a starting material, to ester-forming addition reaction with alkanoic acid monoglycidylester. When, for instance, 2,2-dimethylolbutanoic acid is used, it can be made to react with glycidyl group even without solvent at a comparatively low temperature of about 110° C. or higher. In a reaction at such low temperature, subsidiary reactions such as a reaction between carboxyl group and hydroxyl group and a reaction between hydroxyl group and glycidyl group are hard to occur, and molecular weight distribution comes near to monodispersion infinitely, and, thus, there can be formed a hydroxyl group-containing ester-forming addition reaction product which is very useful for the manufacture of low-solvent or high-solid articles.

As examples of 2,2-dimethylolalkanoic acid of formula (I), there can be mentioned 2,2-dimethylolbutanoic acid, 2,2-dimethylolpentanoic acid and 2,2-dimethylolhexanoic acid, among which 2,2-dimethylolbutanoic acid is preferable.

Another characteristic feature of this invention is to use a specific alkanoic acid monoglycidylester as a reaction partner to the above-mentioned 2,2-dimethylolalkanoic acid. There are known a lot of compounds which have glycidylether group. According to research by the inventors, a reaction between glycidylether and carboxyl group is stoichiometrically hard to proceed, and, resultantly, there remain unreacted compounds as volatile matter, which is undesirable from the viewpoint of cutting down VOC (volatile organic compounds). In this invention, 2,2-dimethylolalkanoic acid of the afore-mentioned formula (I) is made to react with alkanoic acid monoglycidylester of the following formula (II):

(II)

wherein $R^1$ is an alkyl group having 4 to 20, preferably 4 to 13 carbon atoms.

In the above-mentioned formula (II), when the number of carbon atoms of $R^1$ is less than 4, the polarity of thus obtained hydroxyl group-containing ester-forming addition reaction product becomes high, and compatibility with curing agent or the like gets liable to decrease. When, on the other hand, the number of said carbon atoms is more than 20, the hardness of a cured matter which is formed with use of thus obtained hydroxyl group-containing ester-forming addition reaction product gets liable to decrease. Alkyl group $R^1$ in this alkanoic acid monoglycidylester is desirably branched rather than straight-chain. Ester-forming addition reaction product of this invention which is derived from alkanoic acid monoglycidylester of the above-mentioned formula (II) wherein $R^1$ is a branched alkyl group is superior in compatibility with curing agent or the like, and gives cured matter having much higher hardness.

Examples of alkanoic acid monoglycidylester of the above-mentioned formula (II) include pivalic acid glycidylester, hexanoic acid glycidylester, cyclohexanecarboxylic acid glycidylester, 2-ethylhexanoic acid glycidylester, isononanoic acid glycidylester, decanoic acid glycidylester, undecanoic acid glycidylester, lauric acid glycidylester, myristic acid glycidylester, palmitic acid glycidylester, stearic acid glycidylester, "Cardura E 10" (trademark of neodecanoic acid monoglycidylester manufactured by Japan Epoxy Resin Co., Ltd.), "Glydexx N10" (trademark of compound which is mainly composed of neodecanoic acid monoglycidylester, manufactured by Exxon Mobil Corporation) and "Araldite PT910" (trademark of compound which is mainly composed of neodecanoic acid monoglycidylester, manufactured by Ciba-Geigy). These compounds may be used either singly or in combination of two or more species. Among the above-mentioned compounds, pivalic acid glycidylester, cyclohexanecarboxylic acid glycidylester, 2-ethylhexanoic acid glycidylester, isononanoic acid glycidylester, decanoic acid glycidylester, "Cardura E10", "Glydexx N10" and "Araldite PT910" are in particular desirable from the viewpoint of balance between compatibility with curing agent or the like and the hardness of cured matter which is formed from thus obtained hydroxyl group-containing ester-forming addition reaction product.

The hydroxyl group-containing ester-forming addition reaction product of this invention is a product of ester-forming addition reaction between 2,2-dimethylolalkanoic acid of the above-mentioned formula (I) and alkanoic acid monoglycidylester of formula (II), and has an acid value of 20 mgKOH/g or less, preferably 10 mgKOH/g or less, and usually has a hydroxyl value in a range of 300 to 550 mgKOH/g, preferably in a range of 350 to 530 mgKOH/g, and contains, as main ingredients, compounds of the following formula (III) and/or (IV):

(III)

(IV)

wherein $R^1$ and $R^2$ are as defined in the above.

When the acid value of the hydroxyl group-containing ester-forming addition reaction product of this invention exceeds 20 mgKOH/g, unreacted 2,2-dimethylolalkanoic acid undesirably deposits in resin. It is preferable that the hydroxyl group-containing ester-forming addition reaction product of this invention contains unreacted 2,2-dimethylolalkanoic acid and unreacted alkanoic acid monoglycidylester as little as possible, and contains subsidiary reaction products in the possible smallest amount. The hydroxyl group-containing ester-forming addition reaction product of this invention preferably contains therein at least 80% by weight, in particular at least 90% by weight, of the compounds of the above-mentioned formula (III) or (IV).

Compounds of the above-mentioned formula (III) and (IV) are novel compounds which have never been mentioned in any prior literatures, and thus constitute a part of this invention.

The hydroxyl group-containing ester-forming addition reaction product of this invention is produced by the following method.

In detail, according to this invention, 2,2-dimethylolalkanoic acid of the above formula (I) is melted, and the resultant melted matter is mixed with alkanoic acid monoglycidylester of the above formula (II), and is thus subjected to ester-forming addition reaction until the acid value of reaction product becomes 20 mgKOH/g or less, and, thus, a hydroxyl group-containing ester-forming addition reaction product is produced.

In the production method of this invention, 2,2-dimethylolalkanoic acid of the above-mentioned formula (I) which has low melting point and has good solubility in solvent, e.g., 2,2-dimethylolbutanoic acid having a melting point of 110° C., is heated and melted, and the resultant melted matter is allowed to react with alkanoic acid monoglycidylester. Thus, in the method of this invention, reaction can be conducted at a low temperature at which subsidiary reactions can be inhibited, and, furthermore, reaction control is easy, and it is possible to make carboxyl group and glycidyl group react selectively, and, thus, it is possible to form a hydroxyl group-containing ester-forming addition reaction product which resembles monodispersed triol.

When 2,2-dimethylolalkanoic acid of the above formula (I) and alkanoic acid monoglycidylester of the above formula (II) are subjected to ester-forming addition reaction, reaction temperature is preferably in a range of about 110 to about 140° C. from the standpoint of meltability of 2,2-dimethylolalkanoic acid, reaction rate of ester-forming addition reaction, improbableness of subsidiary reaction such as a reaction between hydroxyl group and carboxyl group and difficulty in coloring of reaction product. Although the addition of basic catalyst such as amine can accelerate ester-forming addition reaction, thus produced reaction product is liable to be colored. Reaction is, therefore, preferably conducted without catalyst with a view to obtaining a non-colored or scarcely-colored reaction product.

In the afore-mentioned U.S. Pat. No. 4,314,918, 2,2-dimethylolpropionic acid is not previously melted, and, thus, non-melted 2,2-dimethylolpropionic acid and alkanoic acid monoglycidylester are mixed with each other at one time, and are thus allowed to react. However, 2,2-dimethylolpropionic acid has a melting point as high as 150° C. or more, and, besides, has low solubility in solvent, which requires a reaction at high temperature. Moreover, since 2,2-dimethylolpropionic acid and alkanoic acid monoglycidylester are mixed at one time in this pior art, heat generation occurs so severely that the control of reaction temperature is difficult, and, thus, subsidiary reactions are liable to occur.

In U.S. Pat. No. 5,693,723, 2,2-dimethylolpropionic acid is added four times separately to alkanoic acid monoglycidylester. In this method, however, glycidyl groups are lost as reaction advances, and, therefore, acid value does not ultimately decrease, and, thus, reaction does not sufficiently proceed.

In the production method of this invention, 2,2-dimethylolalkanoic acid is heated and melted, and, then, the resultant melted matter is mixed with alkanoic acid monoglycidylester, and, thus, the resultant mixture is subjected to ester-forming addition reaction at a temperature at which subsidiary reactions can be inhibited. The method of this invention has thus a technically splendid merit that carboxyl group and glycidyl group react selectively, inhibiting the product from becoming high molecular.

2,2-Dimethylolalkanoic acid can be either heated and melted singly or dissolved in a solvent. In the latter case, usable solvent is not restricted in particular. It is preferable, however, that solvent does not react either with reaction product or with starting material. Especially desirable are ester-type and ketone-type solvents which are sufficiently capable of dissolving the above-mentioned 2,2-dimethylolalkanoic acid. When a solvent is used for a reaction in the method of this invention, a part or whole of the solvent may be removed after reaction is over. In this case, it is preferable to use a solvent which can easily be removed. Butyl acetate, isobutyl acetate and methylisobutylketone are in particular suitable in this regard. In the method of this invention, it is also acceptable to dissolve 2,2-dimethylolalkanoic acid either in an organic solvent-solution of resin such as acrylic resin and polyester resin which are usable as resin component of paint, ink, adhesive, etc., or in said resin which contains no organic solvent, and to allow thus dissolved 2,2-dimethylolalkanoic acid to react with the above-mentioned alkanoic acid monoglycidylester.

In the production method of this invention, 2,2-dimethylolalkanoic acid of formula (I) and alkanoic acid monoglycidylester of formula (II) are made to react in such a proportion that the amount of epoxy group in alkanoic acid monoglycidylester of formula (II) is usually 0.8 to 1.5 equivalents, preferably 0.9 to 1.2 equivalents, much desirably 0.95 to 1.1 equivalents, per equivalent of carboxyl group in 2,2-dimethylolalkanoic acid of formula (I), in order that the residue of unreacted matters may remain as little as possible. When 2,2-dimethylolalkanoic acid remains as unreacted matter, it is liable to deposit in reaction product. When, on the other hand, alkanoic acid monoglycidylester remains unreacted, it undesirably acts as a volatile content or a plasticizer.

Furthermore, in the production method of this invention, the ester-forming addition reaction between 2,2-dimethylolalkanoic acid of the above-mentioned formula (I) and alkanoic acid monoglycidylester of formula (II) is preferably conducted until the reaction product has an acid value of 20 mgKOH/g or less, preferably 10 mgKOH/g or less, with a view to inhibiting the deposition of unreacted 2,2-dimethylolalkanoic acid.

The hydroxyl group-containing ester-forming addition reaction product which is produced by the method of this invention contains, as main ingredients, compounds of the afore-mentioned formula (III) and/or (IV). Said product usually contains both of compounds of formula (III) and (IV). The proportion of these two compounds is considered to change according to reaction condition. The objective of this invention is, however, attained regardless of the proportion.

The compounds of formula (III) and (IV) can easily be isolated from the reaction product and purified by any normal method, e.g., a suitable combination of extraction, chromatography, etc.

The afore-mentioned hydroxyl group-containing ester-forming addition reaction product which is produced by this invention has preferably a hydroxyl value in a range of 300 to 550 mgKOH/g, desirably in a range of 350 to 530 mgKOH/g, for the sake of curability when the product is combined with a curing agent into a curable coating composition, and for the sake of compatibility with curing agent etc.

The main ingredients of the hydroxyl group-containing ester-forming addition reaction product of this invention contain, on the one hand, three highly reactive hydroxyl groups and, on the other, have a hydrophobic group with good balance, and, therefore, the product of this invention shows, as a remarkable effect, both curability and compatibility with curing agent.

Triol compounds of the above-mentioned formula (III) or (IV) which are main ingredients of the ester-forming addition reaction product of this invention have low molecular weight, and accordingly have low viscosity, and, furthermore, have high hydroxyl value. Hence, when these triol compounds are to be combined with, for instance, generally low-viscous polyisocyanate curing agent for the purpose of the production of a curable coating composition, it follows that low-viscous polyisocyanate curing agent is necessarily blended in a larger amount with a view to harmonizing the functional equivalent between hydroxyl group and isocyanate group, than in the case where conventional resin having low hydroxyl value is used, with the result that much lower-viscous curable composition can be produced, which is very advantageous for the sake of manufacture of low-solvent articles.

The ester-forming addition reaction product of this invention is therefore advantageously usable as a curable composition in the field of paint, ink, adhesive, etc., and, thus, low-solvent or non-solvent articles such as paint, ink, adhesive, etc. can be manufactured.

This invention thus provides a curable composition which comprises the ester-forming addition reaction product of this invention and a curing agent.

As a curing agent which is to be combined with the ester-forming addition reaction product of this invention, there can be used a curing agent which has a functional group reactive with hydroxyl group. Examples of such a curing agent include polyisocyanate compound, amino resin, acid anhydride group-containing resin, epoxy group-containing resin and alkoxysilyl group-containing resin, among which polyisocyanate compound and amino resin are suitable.

The above-mentioned polyisocyanate compound include both those whose isocyanate group (NCO group) is not blocked (which may hereinafter be abbreviated as "non-blocked polyisocyanate compound") and those whose isocyanate group is blocked (which may hereinafter be abbreviated as "blocked polyisocyanate compound").

Examples of non-blocked polyisocyanate compound include organic polyisocyanate per se, e.g., aliphatic diisocyanates such as lysine diisocyanate, hexamethylene diisocyanate and trimethylhexane diisocyanate; alicyclic diisocyanates such as hydrogenated xylylene diisocyanate, isophorone diisocyanate, methylcyclohexane-2,4 (or 2,6)-diisocyanate, 4,4'-methylenebis(cyclohexylisocyanate) and 1,3-(isocyanatomethyl)cyclohexane; aromatic diisocyanates such as tolylene diisocyanate, xylylene diisocyanate and diphenylmethane diisocyanate; and polyisocyanate of tri- or higher-valence such as lysine triisocyanate, or addition product of each of the above-mentioned organic polyisocyanates with polyvalent alcohol, low molecular polyester resin, water, or the like; or cyclic polymer of the above-mentioned organic diisocyanates with each other (e.g., isocyanurate), or biuret type addition product of the above-mentioned organic diisocyanates; copolymer of isocyanate group-containing ethylenically unsaturated compound such as isocyanatoethyl(meth)acrylate or m-isopropenyl-α,α-dimethylbenzylisocyanate with another ethylenically unsaturated compound.

Blocked polyisocyanate compound has a structure that isocyanate group of the above-mentioned non-blocked polyisocyanate compound is blocked with blocking agent. Suitable examples of said blocking agent include phenolic type ones such as phenol, cresol and xylenol; ε-caprolactam; lactam type ones such as δ-valerolactam, γ-butyrolactam and β-propiolactam; alcohol type ones such as methanol, ethanol, n- or i-propylalcohol, n-, i- or t-butylalcohol, ethyleneglycolmonomethylether, ethyleneglycolmonoethylether, ethyleneglycolmonobutylether, diethyleneglycolmonomethylether, diethyleneglycolmonoethylether, propyleneglycolmonomethylether and benzylalcohol; oxime type ones such as formamidoxime, acetaldoxime, acetoxime, methylethylketoxime, diacetylmonoxime, benzophenone oxime and cyclohexanone oxime; and active methylene type ones such as dimethyl malonate, diethyl malonate, ethyl acetoacetate, methyl acetoacetate and acetylacetone. Isocyanate group of polyisocyanate can easily be blocked by mixing the above-mentioned non-blocked polyisocyanate with the above-mentioned blocking agent.

These polyisocyanate compounds can be used either singly or in combination of two or more species.

Examples of the above-mentioned amino resin include methylol amino resin which is obtained by a reaction between amino component such as melamine, urea, benzoguanamine, acetoguanamine, stearoguanamine, spiroguanamine and dicyandiamide, and aldehyde. Said amino resin also includes methylol melamine resin which has been etherified with one or more species of alcohol, preferably $C_1$ to $C_4$ monohydric alcohol. In particular suitable is melamine resin which is prepared by etherifying at least a part of methylol groups of methylol melamine resin with $C_1$ to $C_4$ monohydric alcohol.

In the curable composition of this invention, ester-forming addition reaction product and the above-mentioned curing agent are blended with each other in such a manner that the weight ratio of solid content of ester-forming addition reaction product/curing agent may fall within a range of 80/20 to 20/80, preferably 70/30 to 30/70, much desirably 60/40 to 35/65.

Furthermore, if necessary, curing catalyst, pigment and fluidity modifier may be blended with the curable composition of this invention. The curable composition of this invention can be used for paint, ink, adhesive, etc. The curing condition for the curable composition of this invention may be suitably decided according to the species of curing agent or the use of the curable composition. When the curable composition is to be used for paint, preferable curing condition is usually 10 to 40 minutes at a temperature ranging from about 100 to about 180° C.

In the following, this invention is explained in more detail with Examples and Comparative Examples. Part and % are based on weight. The thickness of coating film means the thickness of cured film.

Production of Hydroxyl Group-Containing Ester-Forming Addition Reaction Product

EXAMPLE 1

A reactor equipped with stirrer, cooler, temperature controller, nitrogen-introducing tube and dropping funnel was fed with 296 parts of 2,2-dimethylolbutanoic acid. The air in the reactor was replaced with nitrogen, and, then, said 2,2-dimethylolbutanoic acid was heated to 120° C. and melted. To thus melted matter, 490 parts of "Cardura E10" (trademark of Japan Epoxy Resin Co., Ltd., mainly composed of neodecanoic acid monoglycidyl ester) was added dropwise over a period of two hours, with the temperature maintained at 120° C. When acid value became 9 or lower, the reaction was terminated, and, thus, hydroxyl group-containing ester-forming addition reaction product (A-1) was obtained. This hydroxyl group-containing ester-forming addition reaction product (A-1) had a solid content of about 98%, a Gardner-Holdt viscosity (20° C.) of $Z_6Z_7$, a color number of 1, a hydroxyl value of 428 mgKOH/g, a number average molecular weight of 600, a weight average molecular weight of 610 and Mw/Mn of 1.02. Number average molecular weight and weight average molecular weight were determined by gel permeation chromatography (GPC) (the same applies in the following).

Figure 1:
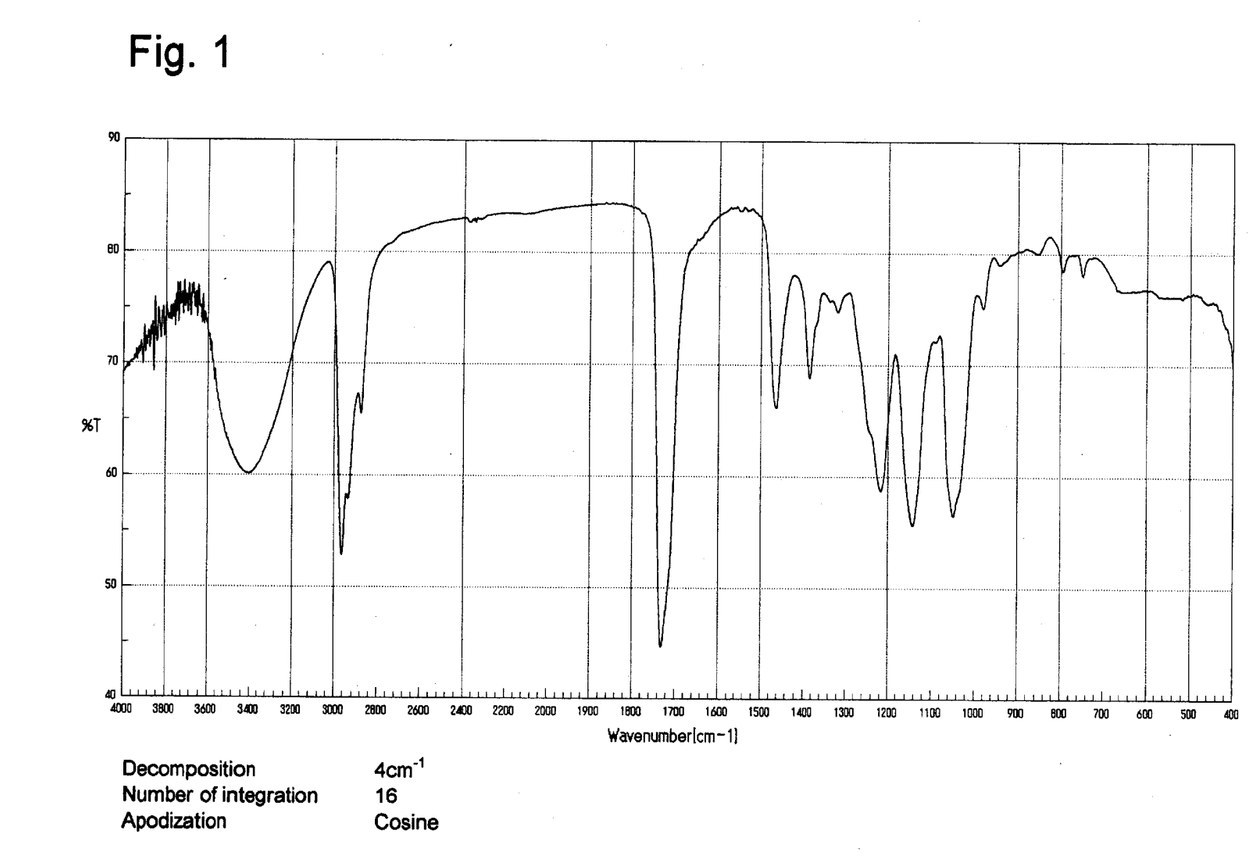
Figure 2:
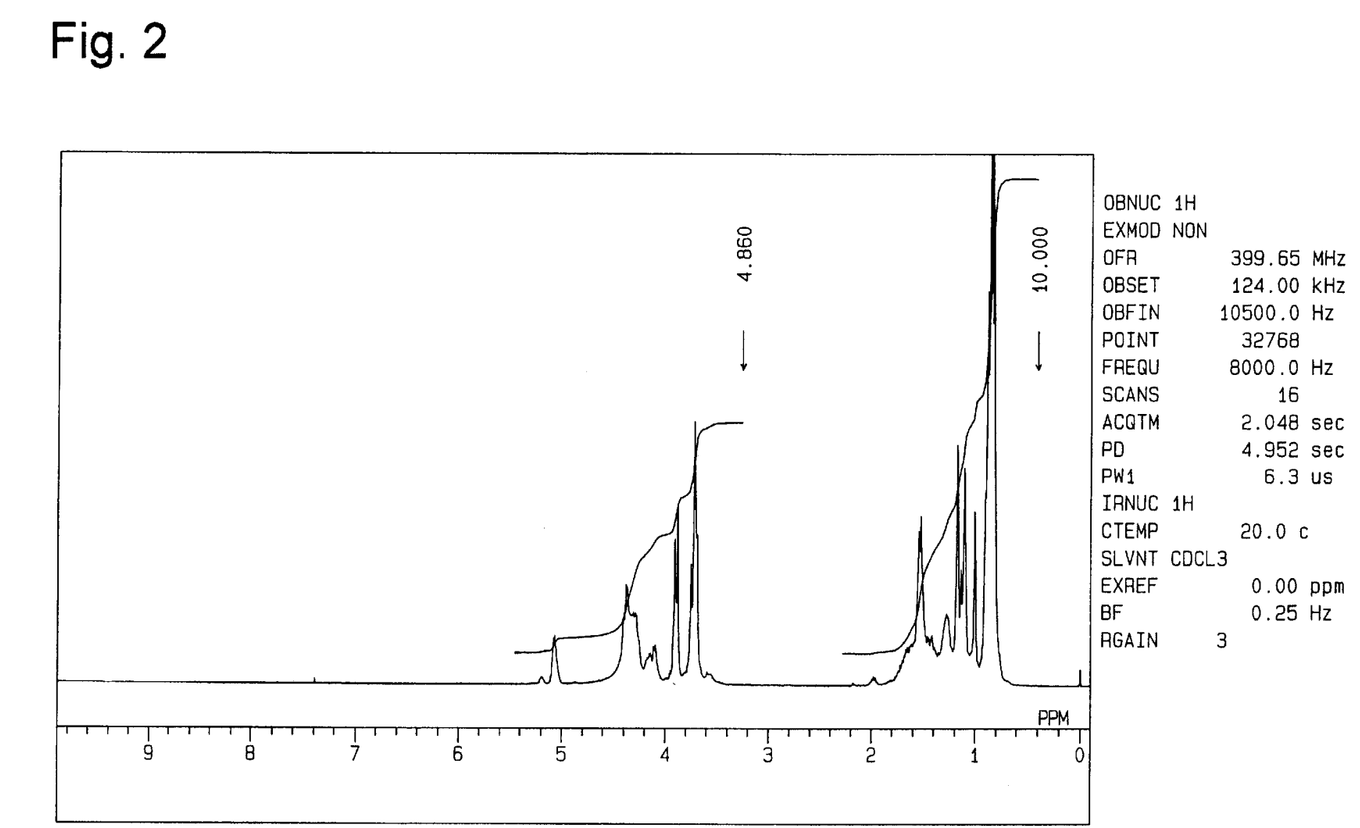
Figure 3:
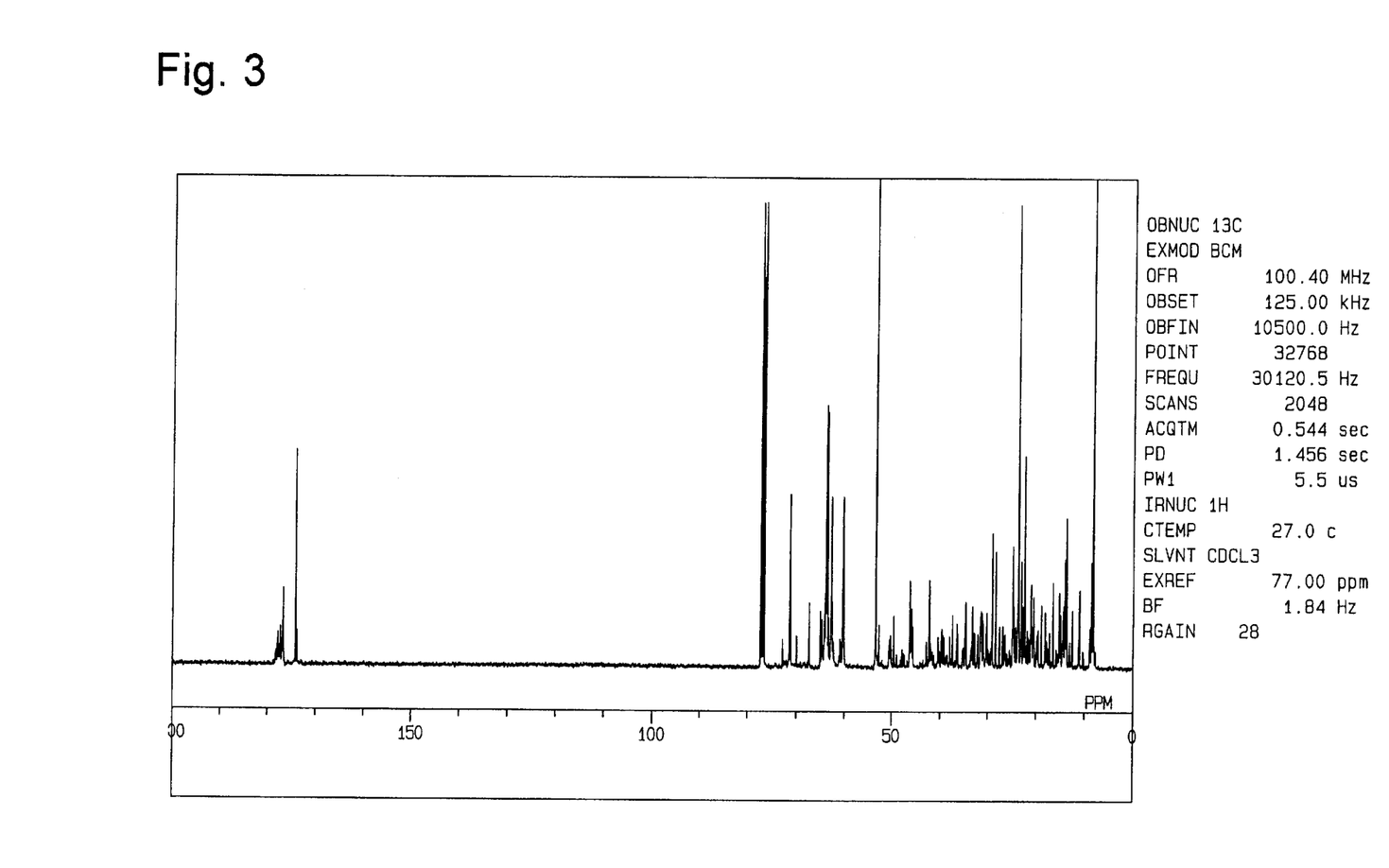

IR analysis chart (FIG. 1), $^1$H-NMR analysis chart (in heavy chloroform, room temperature, 0 to 10 ppm) (FIG. 2) and $^{13}$C-NMR analysis chart (in heavy chloroform, room temperature, 0 to 200 ppm) (FIG. 3) are attached hereto.

NMR analysis showed that hydroxyl group-containing ester-forming addition reaction product (A-1) contained about 22% by weight of the compound of formula (III) wherein $R^1$ denotes an alkyl group having 8 to 10 carbon atoms and $R^2$ is an ethyl group, and about 75% by weight of the compound of formula (IV) wherein $R^1$ denotes an alkyl group having 8 to 10 carbon atoms and $R^2$ is an ethyl group.

EXAMPLE 2

The same reactor as in Example 1 was fed with 296 parts of 2,2-dimethylolbutanoic acid and 197 parts of isobutylacetate. The air in the reactor was replaced with nitrogen, and, then, the content of the reactor was heated to 120° C. and melted. To thus melted matters, 490 parts of "Cardura E10" was added dropwise over a period of two hours, with the temperature maintained at 120° C. When acid value became 9 or lower, the reaction was terminated, and, then, isobutylacetate was removed by pressure reduction, and, thus, hydroxyl group-containing ester-forming addition reaction product (A-2) was obtained. This hydroxyl group-containing ester-forming addition reaction product (A-2) had a solid content of about 98%, a Gardner-Holdt viscosity (20° C.) of $Z_6Z_7$, a color number of 1, a hydroxyl value of 428 mgKOH/g, a number average molecular weight of 600, a weight average molecular weight of 610 and Mw/Mn of 1.02.

NMR analysis showed that hydroxyl group-containing ester-forming addition reaction product (A-2) contained about 22% by weight of the compound of formula (III) wherein $R^1$ denotes an alkyl group having 8 to 10 carbon atoms and $R^2$ is an ethyl group, and about 75% by weight of the compound of formula (IV) wherein $R^1$ denotes an alkyl group having 8 to 10 carbon atoms and $R^2$ is an ethyl group.

EXAMPLE 3

The same reactor as in Example 1 was fed with 296 parts of 2,2-dimethylolbutanoic acid and 197 parts of ethyl-3-ethoxypropionate. The air in the reactor was replaced with nitrogen, and, then, the content of the reactor was heated to 120° C. and melted. To thus melted matters, 490 parts of "Cardura E10" was added dropwise over a period of two hours, with the temperature maintained at 120° C. When acid value became 9 or lower, the reaction was terminated, and, thus, hydroxyl group-containing ester-forming addition reaction product (A-3) was obtained. This hydroxyl group-containing ester-forming addition reaction product (A-3) had a solid content of about 77%, a Gardner-Holdt viscosity (20° C.) of QR, a color number of 1, a hydroxyl value of 430 mgKOH/g, a number average molecular weight of 590, a weight average molecular weight of 600 and Mw/Mn of 1.02.

NMR analysis showed that hydroxyl group-containing ester-forming addition reaction product (A-3), except for solvent, contained about 23% by weight of the compound of formula (III) wherein $R^1$ denotes an alkyl group having 8 to 10 carbon atoms and $R^2$ is an ethyl group, and about 74% by weight of the compound of formula (IV) wherein $R^1$ denotes an alkyl group having 8 to 10 carbon atoms and $R^2$ is an ethyl group.

COMPARATIVE EXAMPLE 1

The same reactor as in Example 1 was fed with 490 parts of "Cardura E10", and the air in the reactor was replaced with nitrogen, and, then, the content of the reactor was heated to 120° C. Then, 296 parts of 2,2-dimethylolbutanoic acid was added to the content in the reactor 8 times separately over a period of two hours. After the addition was over, the temperature was maintained at 120° C. for three hours, and, thus, acid value was determined. However, acid value had decreased only to 75 mgKOH/g, and almost no epoxy group remained. When the reactor was cooled, a large amount of 2,2-dimethylolbutanoic acid deposited.

COMPARATIVE EXAMPLE 2

The same reactor as in Example 1 was fed with 490 parts of "Cardura E10" and 67 parts of 2,2-dimethylolpropionic acid. The air in the reactor was replaced with nitrogen, and, then, the content of the reactor was heated to 130° C. Although heat generation started after a while, the temperature was maintained at 130° C. Then, further 67 parts of 2,2-dimethylolpropionic acid was added three times in total over a period of four hours. After the addition was over, the temperature was maintained at 150° C. for three hours, and, thus, acid value was determined. However, acid value had decreased only to 70 mgKOH/g, and almost no epoxy group remained. When the reactor was cooled, a large amount of 2,2-dimethylolpropionic acid deposited.

COMPARATIVE EXAMPLE 3

The same reactor as in Example 1 was fed with 292 parts of adipic acid. The air in the reactor was replaced with nitrogen, and, then, the content of the reactor was heated to 150° C. and melted. To thus melted matter, 490 parts of "Cardura E10" was added dropwise over a period of two hours, with the temperature maintained at 150° C. When acid value became 9 or lower, the reaction was terminated, and, thus, hydroxyl group-containing ester-forming addition reaction product (C-3) was obtained. This hydroxyl group-containing ester-forming addition reaction product (C-3) had a solid content of about 98%, a Gardner-Holdt viscosity (20° C.) of $Z_6$, a color number of 1, a hydroxyl value of 176 mgKOH/g, a number average molecular weight of 800, a weight average molecular weight of 910 and Mw/Mn of 1.13.

Preparation of Test Samples and Test

As mentioned in each of the following Preparation Examples 1 to 4, there were prepared test samples of clear paint which had been diluted with propyleneglycol monomethylether acetate so that viscosity by Fordcup #4 at 20° C. might be 60 seconds, and, thus, the test samples were used for test.

PREPARATION EXAMPLE 1

There were mixed 100 parts of hydroxyl group-containing ester-forming addition reaction product (A-1) obtained in Example 1 and 150 parts of "Sumidur N-3300" (trademark of polyisocyanate manufactured by Sumitomo Bayer Urethane Co., Ltd.), and, then, the resultant mixture was diluted with propyleneglycol monomethylether acetate, and, thus, there was obtained clear paint whose viscosity by Fordcup #4 (20° C.) was 60 seconds.

PREPARATION EXAMPLE 2

Preparation Example 1 was repeated except that hydroxyl group-containing ester-forming addition reaction product (A-1) obtained in Example 1 was replaced with hydroxyl group-containing ester-forming addition reaction product (A-2) obtained in Example 2, and, thus, there was obtained clear paint whose viscosity by Fordcup #4 (20° C.) was 60 seconds.

PREPARATION EXAMPLE 3

Preparation Example 1 was repeated except that hydroxyl group-containing ester-forming addition reaction product (A-1) obtained in Example 1 was replaced with hydroxyl group-containing ester-forming addition reaction product (A-3) obtained in Example 3 in accordance with the formulation as shown in Table 1 which is mentioned later, and, thus, there was obtained clear paint whose viscosity by Fordcup #4 (20° C.) was 60 seconds.

PREPARATION EXAMPLE 4 (FOR COMPARISON)

There were mixed 100 parts of hydroxyl group-containing ester-forming addition reaction product (C-3) obtained in Comparative Example 3 and 62 parts of "Sumidur N-3300", and, then, the resultant mixture was diluted with propyleneglycol monomethylether acetate, and, thus, there was obtained clear paint whose viscosity by Fordcup #4 (20° C.) was 60 seconds.

PREPARATION EXAMPLE 5 (FOR COMPARISON)

There were mixed 100 parts of PLACCEL303 (polycaprolactone polyol having a hydroxyl value of 540 mgKOH/g, manufactured by Daicel Chemical Industries, Ltd.) and 190 parts of "Sumidur N-3300". These compounds were however incompatible, and, therefore, no test could be conducted.

Clear paint samples which had been obtained in the above-mentioned Preparation Examples 1 to 4 were tested for coating film hardness and for the content of residue after heating, by the following test method. Results are shown in Table 1 which is mentioned later.

Test Method

Coating Film Hardness:

Clear paint was applied on a tinplate so that the thickness of dried coating film might be 40 μm, and was then baked by a heating drier at 140° C. for 30 minutes. After left still in a room at 20° C. for 24 hours, the resultant coating film was measured for coating film hardness by a Knoop hardness tester. The larger the measurement value is, the harder is the coating film.

The Content of Residue after Heating:

About 0.5 g of clear paint was put in an aluminum dish, and was heated at 110° C. for one hour. The content of residue of clear paint after heating was found from the weight before and after heating, in accordance with the following formula:

$$\text{The content of residue after heating } (\%) = [(W2-W0)/(W1-W0)] \times 100$$

W0: the weight of aluminum dish

W1: the total weight of clear paint and aluminum dish before heating

W2: the total weight of solidified clear paint and aluminum dish after heating

TABLE 1

| Preparation Example No. | 1 | 2 | 3 | 4 | 5 |
|---|---|---|---|---|---|
| Hydroxyl group-containing resin (A-1) | 100 | | | | |
| Hydroxyl group-containing resin (A-2) | | 100 | | | |
| Hydroxyl group-containing resin (A-3) | | | 125 | | |
| Hydroxyl group-containing resin (C-3) | | | | 100 | |
| PLACCEL303 | | | | | 100 |
| Sumidir N-3300 | 150 | 150 | 150 | 62 | 190 |
| Propyleneglycol monomethylether acetate | Suitable amount | Suitable amount | Suitable amount | Suitable amount | — |
| VOC (lbs/gal) | 1.71 | 1.70 | 1.75 | 2.03 | — |
| Non-volatile content (weight %) | 81.0 | 81.1 | 80.6 | 77.4 | — |
| Coating film hardness (KHN) | 11.6 | 11.6 | 11.7 | 3.2 | — |

As is clearly seen in the above-mentioned Examples, the hydroxyl group-containing ester-forming addition reaction product of this invention is very useful for the manufacture of low-solvent curable composition, and, furthermore, has good compatibility with curing agent, and gives sufficient hardness. Besides, the production method of this invention by which to melt 2,2-dimethylolalkanoic acid and add alkanoic acid monoglycidylester to the resultant melted matter attains easy control of reaction, makes it possible to allow carboxyl group and glycidyl group to react selectively, and is thus capable of producing a hydroxyl group-containing ester-forming addition reaction product which comprises almost mono-dispersed triol.

What is claimed is:

1. A reaction product of ester-forming addition reaction between 2,2-dimethylolalkanoic acid of the following formula (I):

(I)

wherein $R^2$ is an alkyl group having 2 to 4 carbon atoms, and alkanoic acid monoglycidylester of the following formula (II):

(II)

wherein $R^1$ is an alkyl group having 4 to 20 carbon atoms, which product has an acid value of 20 mgKOH/g or less.

2. The reaction product of claim 1 wherein 2,2-dimethylolalkanoic acid of formula (I) is 2,2-dimethylolbutanoic acid.

3. The reaction product of claim 1 wherein $R^1$ in formula (II) is a branched alkyl group having 4 to 13 carbon atoms.

4. The reaction product of claim 1 wherein alkanoic acid monoglycidylester of formula (II) is selected from the group consisting of pivalic acid glycidylester, cyclohexanoic acid glycidylester, 2-ethylhexanoic acid glycidylester, isononanoic acid glycidylester, decanoic acid glycidylester, Cardura E10, Glydexx N10 and Araldite PT910.

5. The reaction product of claim 1 wherein the acid value is 10 mgKOH/g or less.

6. The reaction product of claim 1 wherein the hydroxyl value is in a range of 300 to 550 mgKOH/g.

7. Compounds of formula (III) or (IV) as follows:

(III)

-continued (IV)

wherein $R^1$ is an alkyl group having 4 to 20 carbon atoms, and wherein $R^2$ is an alkyl group having 2 to 4 carbon atoms.

8. A process to produce the ester-forming addition reaction product of claim 1, which process is characterized in that 2,2-dimethylolalkanoic acid of the following formula (I):

(I)

wherein $R^2$ is an alkyl group having 2 to 4 carbon atoms, and alkanoic acid monoglycidylester of the following formula (II):

(II)

wherein $R^1$ is an alkyl group having 4 to 20 carbon atoms, are subjected to an ester-forming addition reaction until the acid value of the resultant reaction product becomes 20 mgKOH/g or less.

9. The process of claim 8 wherein the ester-forming addition reaction is conducted at a temperature ranging from 110 to 140° C. without catalyst.

10. The process of claim 8 wherein 2,2-dimethylolalkanoic acid of formula (I) and alkanoic acid monoglycidylester of formula (II) are subjected to an ester-forming addition reaction in such a proportion that the amount of epoxy group in the alkanoic acid monoglycidylester is 0.8 to 1.5 equivalents per equivalent of carboxyl group in the 2,2-dimethylolalkanoic acid.

11. A curable composition which comprises the ester-forming addition reaction product of claim 1 and a curing agent.

* * * * *